United States Patent [19]

Gerken

[11] Patent Number: 4,961,351
[45] Date of Patent: Oct. 9, 1990

[54] FILLABLE SAMPLE TAKING VESSEL FOR HANDLING A LIQUID SAMPLE

[75] Inventor: Hero Gerken, Hamburg, Fed. Rep. of Germany

[73] Assignee: Firma Eppendorf-Netheler-Hinz GmbH, Fed. Rep. of Germany

[21] Appl. No.: 311,526

[22] Filed: Feb. 16, 1989

[30] Foreign Application Priority Data

Mar. 9, 1988 [DE] Fed. Rep. of Germany ....... 3807704

[51] Int. Cl.$^5$ .............................................. G01N 1/12
[52] U.S. Cl. ................................................. 73/864.65
[58] Field of Search ............ 73/864.65, 864.11, 864.13, 73/864.16, 864.73, 864.63; 251/318, 319; 422/100

[56] References Cited

U.S. PATENT DOCUMENTS

| 540,121 | 5/1895 | Tagiabue | 73/864.65 |
| 1,621,857 | 3/1927 | Seraphin | 73/864.65 |
| 2,678,563 | 5/1954 | Parrish | 73/864.65 |
| 3,169,322 | 2/1965 | Milo | 73/864.65 |
| 3,390,463 | 7/1968 | Hirsch | 73/864.65 |
| 4,197,746 | 4/1980 | Hack et al. | 73/825.4 |
| 4,367,657 | 1/1983 | Ward | 73/864.65 |
| 4,760,747 | 8/1988 | Fackler | 73/864.65 |

FOREIGN PATENT DOCUMENTS

| 0273057 | 7/1988 | European Pat. Off. . |
| 859684 | 12/1952 | Fed. Rep. of Germany . |
| 2658592 | 11/1977 | Fed. Rep. of Germany . |
| 3029718 | 8/1980 | Fed. Rep. of Germany . |
| WO87/07728 | 12/1987 | PCT Int'l Appl. . |

OTHER PUBLICATIONS

Patent Abstracts of Japan, vol. 7, No. 109 (P-196)[1254], May 12, 1983; JP-A-58-32137.

Primary Examiner—Hezron E. Williams
Attorney, Agent, or Firm—Toren, McGeady & Associates

[57] ABSTRACT

A fillable sample taking element for handling a liquid sample has a conical end portion which defines an intake and discharge opening, which is adapted to be sealed by a conical valve member, which is provided with an actuating rod, which protrudes outwardly through the intake opening and is bare relative to said intake opening. The valve constitutes a gravity valve having a valve member (8) which is disposed in the interior of the sample taking element (3) in the tapering portion (13) thereof which is disposed above and tapers from the intake opening (6). The valve seat for that valve member has a surface which faces away from the intake and discharge opening. The outwardly protruding actuating rod (10) serves to unseat the valve member. The valve will be closed when the sample taking element is arranged with the intake and discharge opening at the bottom and/or under the action of an internal pressure in the sample taking element.

8 Claims, 5 Drawing Sheets

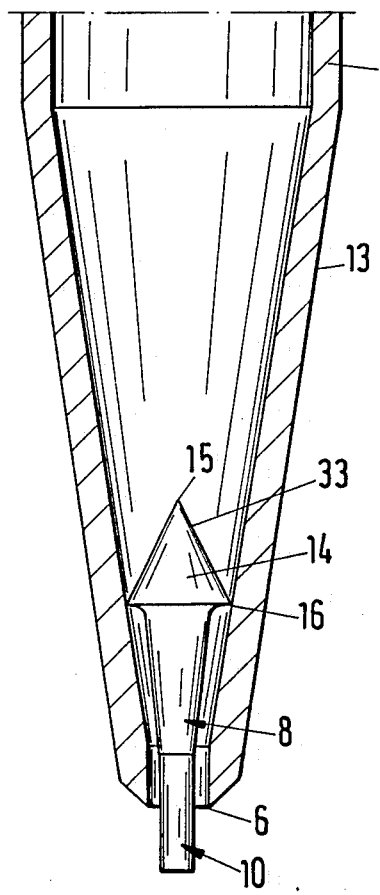
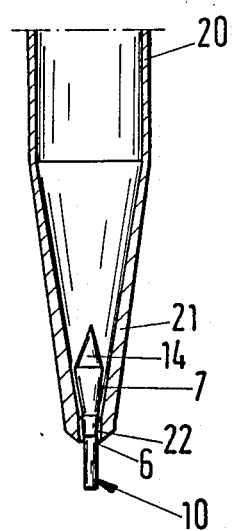
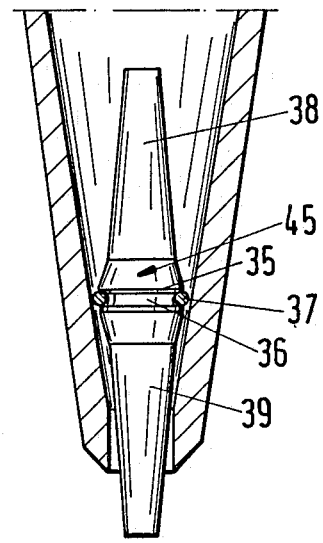

FILLABLE SAMPLE TAKING VESSEL FOR HANDLING A LIQUID SAMPLE

BACKGROUND OF THE INVENTION

1. Field of the Invention

This invention relates to a fillable sample taking vessel for handling a liquid sample, particularly a vessel for use as a pipette tip, which vessel has an opening which is relatively large in cross-section at one end, where the vessel is relatively large in diameter, and tapers in conical shape to the other end and is formed there with an intake and discharge opening (to be described as an intake opening hereinafter), wherein a movable valve member for sealing the intake opening is provided adjacent to the intake opening and is provided with an actuating rod, which protrudes out through the intake opening and is bare relative to the intake opening.

In a special embodiment the invention includes a sample taking vessel in which the opening which is relatively large in cross-section is defined by a cylindrical wall portion and in which a piston which has been inserted through the relatively large opening has an outwardly extending piston rod, and which sample taking vessel is optionally provided with a flange at the end which is relatively large in cross-section.

In that context the invention provides also a process of handling a liquid sample in a sample taking vessel which is conical at least in part and has a tip that is provided with an opening which constitutes an intake opening or also a discharge opening.

2. Description of the Prior Art

A fillable sample taking vessel of the kind described hereinbefore is known from Published German Application No. 30 29 718. For the transport of liquids to be analyzed, that sample vessel can be sealed at its bottom after the liquid has been sucked into the vessel. It is intended to seal the vessel by an operation performed with one hand. For this reason the known embodiment comprises the downwardly protruding actuating rod.

In the embodiment comprising a movable valve member a valve seat is provided within the vessel close to the intake opening and the valve member can be seated on that valve seat in that the actuating rod is forced against an abutment. As a result, the valve member is non-detachably connected to the valve seat for the further manipulation and/or an irreversible snap-action joint is established so that the filled sample vessel is sealed at its bottom as it is transferred to a different location and no liquid can escape even when the suction has been discontinued.

When the bottom intake opening has been sealed and liquid is subsequently to be dispensed, it will be necessary to detach the sample vessel from a pipette or a similar device, depending on the embodiment, and to take out or pour the liquid from the top. That operation is time-consuming and complicated and a satisfactory operation requires special skill and time. That known embodiment has mainly been provided in order to reliably hold in the sample vessel a liquid which has been received by the vessel.

It is known to provide valves on pipettes rather than on sample vessels which can be fitted on pipettes. German Patent Publication No. 22 29 623 discloses a valve and a throttling bore in the pipette, specifically in a special guide piece, in order to provide an air duct for retarding the upward movement of the piston of the pipette so that the sample vessel proper will be filled uniformly and without splashing. That arrangement has the object to provide a particularly simple pipette, which can infinitely and linearly be adjusted to various volumes and can be calibrated also for various liquids. The so-called fit-on pipette tube, which is comparable to the sample vessel, is provided in the usual manner without any additional features.

In accordance with Published German Application No. 26 58 592 a pipette for mixing a liquid with another liquid, which has been taken up by a pipetting action, is provided with valve means for controlling the intake of liquid and for contacting the two liquids with each other.

Those valve means are contained in a special pipette, which has a complicated design, rather than in a sample taking vessel, and is not related to a valve for controlling an intake opening of a sample taking or fit-on vessel or a tiplike vessel assembly, which is provided with a piston.

SUMMARY OF THE INVENTION

It is an object of the invention so to improve a sample taking vessel which is of the kind described first hereinbefore that a sample, particularly one having a relatively high vapor pressure, can be taken through the intake opening and be held in the sample taking vessel, and that it is possible by a one-hand actuation and in conjunction with the actuating device, which may consist of a pipette or a pipetting device for actuating a syringe which is associated with a sample holding vessel, to transfer the vessel to a different location and to dispense the contents of the vessel in a simple manner and, if desired, in controlled quantities.

This object is accomplished in accordance with the invention in that a gravity valve is provided, which has a valve member that is disposed inside the sample taking vessel in its tapering portion above the intake opening, and which cooperates with a valve seat so as to seal the intake opening and is disposed on that side of said valve seat which faces the relatively large opening, and the outwardly protruding actuating rod is operable to unseat the valve member.

The term gravity valve indicates that when the sample taking vessel is held in a proper orientation that valve will act as a check valve. In a sample taking vessel of the kind described hereinbefore the provision of a gravity valve will afford the advantage that even without additional features and with agravity valve which can repeatedly be used and can be inserted and removed through the opening at the top of the sample taking vessel and that sample taking vessel can be used to transport a sample liquid to various locations and when used at a given location precludes a dripping even when a sample liquid having a high vapor pressure is being handled. That vapor pressure gives rise to an internal pressure and the reference thereto includes that the invention is particularly directed to the handling of relative large volumes of liquid in the sense indicated, also together with air as an interposed fluid. In amounts having relatively large volumes, organic substances and liquids having a relatively high vapor pressure will generate an internal pressure, which in known processes and sample taking vessels results in a change of the volume because liquid is dripped. This remark includes not only the use for medical purposes but also the technical use in analytical chemistry. These are preferred uses of the vessel in accordance with the invention.

Liquids having a relatively high vapor pressure, particularly organic substances or organic liquids, can be handled to special advantage by the vessel in accordance with the invention. This includes also all aggressive substances, such as acids. A special use relates to the processing of large volumes of liquids having high vapor pressures. The term "relatively large volumes" is used herein to describe volumes in excess of 1 milliliter. This is an additional feature of the invention.

The reference to a gravity valve involves that the function of such valve may be controlled by a vapor pressure which develops when the sample liquid has been taken by the vessel, particularly because in a sample vessel that has been fitted on a pipette the holding space is limited at its top by the components of the pipette.

The valve member of the gravity valve may particularly be made of an inert material, which may consist of metal, special steel, glass plastic or ceramic. This is also included as a particularly advantageous feature. In connection with the term "gravity valve" it is pointed out that the valve member has a higher specific gravity than water or a halogenated hydrocarbon which is to be handled so that the valve member will not float in the sample liquid to be handled by the vessel.

The invention relates to the above-mentioned sample taking vessel as well as a valve member, which constitutes a gravity valve and can freely be inserted into and removed from such sample taking vessel.

In accordance with the remarks made hereinbefore the vessel may be similar to a tip provided with a piston. In that case the vessel may also have a tapering conical sealable end portion that is provided with the intake opening and contains the valve. Hereinafter the reference to a sample vessel will include also the stated embodiments.

In a suitable embodiment the valve seat is constituted by an inwardly directed step, which is formed in the sample taking vessel and particularly has a flat top. Such step will require a special design of the sample vessel. In that context and also without that restricting feature the valve seat preferably has the shape of an upwardly flaging cone, which is adapted to receive a mating conical portion of the valve member. In a particularly desirable embodiment a conical valve seat is constituted by the inside surface of a tapering wall portion of the sample vessel. In that case the valve member conform to the taper of the vessel and may be used also with conventionally shaped vessels.

Whereas the conical portion may adjoin an annular flange, a special embodiment includes a valve seat which has a flat top surface that cooperates with a valve member that consists of a cylindrical disk.

In a particularly preferred embodiment, the valve member is disposed at the inner end of a displaceable stem, which is provided with the actuating rod, and the valve member has a rim which cooperates with a valve seat that is constituted by a conically tapering wall portion of the sample vessel. This constitutes a special embodiment, in which the seat of the gravity valve which seals the sample vessel at its bottom is spaced above the intake opening. In a desirable embodiment the valve member consists of a cone having an apex which faces into the interior of the sample vessel and said cone has a base rim which constitutes the seating portion of the valve member.

In that case and in the other embodiments described hereinbefore a desirable feature resides in that the seating portion of the valve member is resiliently deformable and is particularly provided with resilient sealing inserts. In such an embodiment the valve seat having the wedge-shaped taper can particularly favorably be designed in view of special sealing requirements and also draining requirements.

In view of the fact that the valve member cooperates with a valve seat near or slightly above the intake opening, the valve member may be provided above its seating portion with an extension, which is directed into the interior of the sample vessel and has an outwardly protruding pilot rim or element. Even when the sample vessel and a pipette holding that vessel are held in an inclined position that design will ensure that the valve member will not be canted so that it will be clamped in a manner which will prevent the required sealing of the sample vessel. The pilot element may be star-shaped and formed with laterally or centrally disposed passages. If the pilot element is star-shaped, its outer tips will have a high flexibility.

The overall length of the valve member desirably exceeds the diameter of the relatively large opening. This will increase the reliability in operation.

As the valve member is inserted, it must be moved to a defined position and will then be held in its correct position.

In a preferred embodiment the rim of the pilot element and particularly of the extension of the valve member is bare relative to the wall of the sample vessel at that cross-section of the sample vessel at which that rim is disposed when the valve is closed.

Even if a pilot element is provided, the extension preferably consists of a cone having an apex that faces the top end of the sample vessel. That apex will afford the advantage that a centering guidance will be affected under the action of a liquid acting by gravity or under the action of a vapor pressure because the pressure-applying influences will be deflected toward the periphery on all sides.

The provision of the extension permits a simple determination of the length of the valve member. Even when the sample vessel or a pipette carrying that vessel is held with an inclination, the valve member will not be canted so as to be clamped in a manner which will prevent the required sealing of the sample vessel at its bottom end.

In a suitable embodiment the actuating rod consists of a cone that constitutes also a valve member.

In another desirable embodiment the actuating rod has below the valve member a portion which is bare relative to the intake opening and which constitutes a pilot element and the outwardly protruding end portion of the actuating member is smaller in cross-section than said bare portion. That design will result in a particularly compact embodiment. In general, the sample vessel comprises a freely movable valve member, which has been inserted from the top of the vessel and can repeatedly be used.

In a special design, such valve member comprises a cylindrical intermediate portion and at both ends of said cylindrical portion is provided with conical portions which terminate in conical tips, one of which constitutes or is provided with an actuating rod.

In a particularly desirable embodiment the two end portions of the valve member directly adjoin an intermediate portion formed with the seating rim are conical so that an annular drain opening which is as large as possible will be obtained when said rims contact the wall of the vessel.

In connection with the above reference to volumes in excess of 1 milliliter in connection with the vapor pressure, it is pointed out that special advantages will be afforded by the use of the sample baking vessel for handling large volumes of an order of, e.g., 1 to 50 milliliters, particularly 1 to 10 milliliters, in analytical work. This will constitute a special embodiment of the invention. With that feature the intake and/or discharge opening of a sample taking vessel, in dependence on its orientation, may be sealed if said opening is disposed at the bottom of the vessel and/or under an internal pressure and by a one-hand operation of the device said vessel may be opened to discharge its contents in that an external force is exerted which is directed toward the intake opening.

In connection with the reference to an internal pressure the invention is particularly directed to the handling of relatively large volumes as defined hereinbefore, also together with air used as an intermediate fluid.

It has been explained hereinbefore that particularly organic substances and liquids having relatively high vapor pressures in volumes in excess of a certain limit will generate an internal pressure which in known vessels results in a dripping, which is undesirable because the volume is changed and because damage may result in dependence on the nature of the liquid. In the handling of liquids having a higher vapor pressure than water and tending to drip, particularly of such organic liquids, the seal is suitably effected by gravity in dependence on the orientation of the vessel, and under the action of a vapor pressure which develops in the interior. In that case the valve will be opened by an action exerted on the outside against the internal pressure in the vessel. For this reason that process can be carried out with simple means.

BRIEF DESCRIPTION OF THE DRAWING

FIG. 2 is a fragmentary vertical sectional view showing the bottom end portion of an embodiment of the sample vessel.

FIG. 2a illustrates a modification of FIG. 2 with an additional resilient sealing element.

FIG. 4 is a fragmentary view which is similar to FIG. 2 and shows a different sample vessel, which constitutes a different embodiment of the invention.

DETAILED DESCRIPTION OF THE PREFERRED EMBODIMENTS

Figure 1:
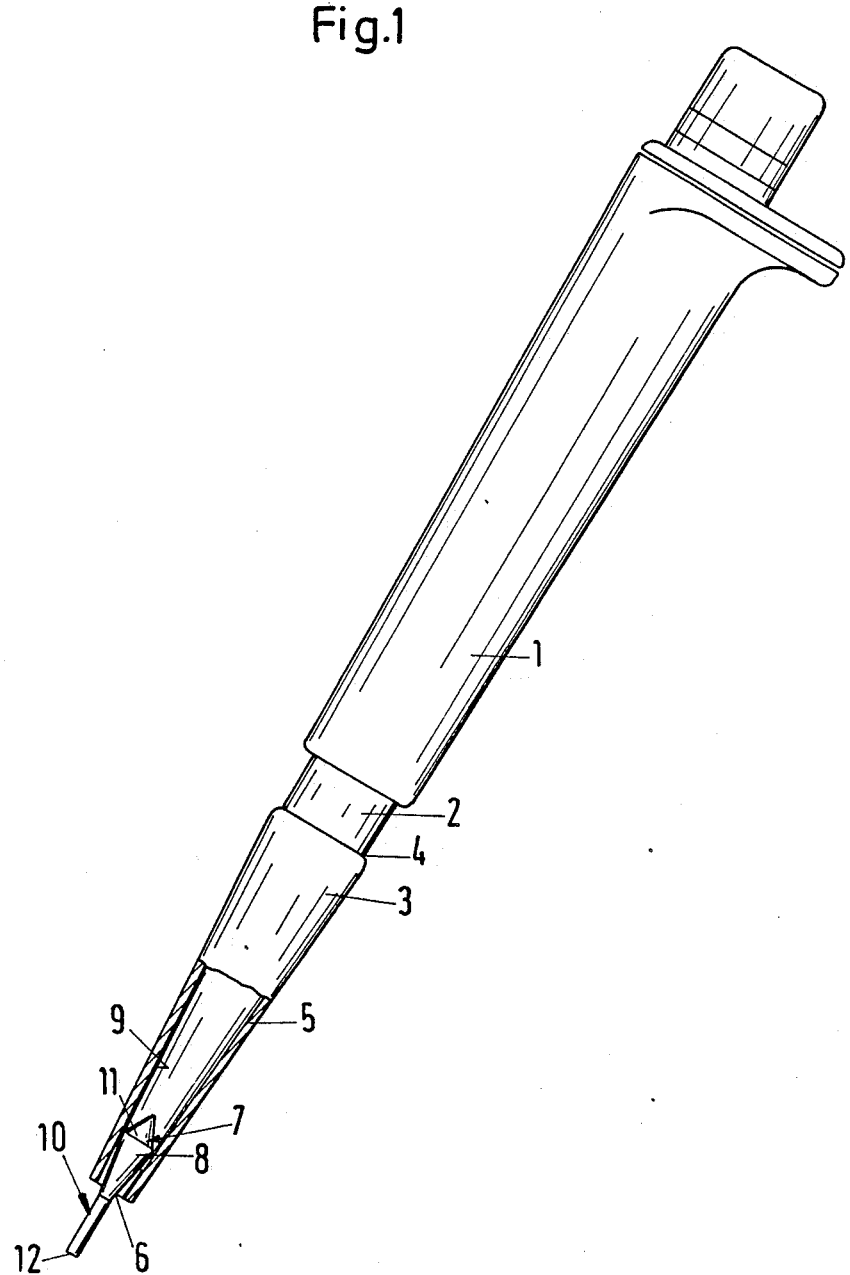
FIG. 1 is a diagrammatic side elevation showing a pipette and a sample vessel fitted thereon.

The invention will be described hereinafter with reference to illustrative embodiments which are shown on the drawing on different greatly enlarged scales.

When reference is made hereinafter to a sample vessel, that term is intended to include also a different sample taking element which adjacent to the receiving and discharge opening or the so-called intake opening has a similar design. The term intake opening is not used in a restricting sense but includes also openings through which a discharge may be effected.

The pipette 1 shown in FIG. 1 has the usual design, e.g., in accordance with German Patent Specification No. 25 49 477. That pipette has at its bottom a fitting cone 2, on which the top opening 4 of a sample vessel 3 has been fitted. That sample vessel is conical at least in part at its top and bottom and comprises a downwardly tapering wall portion 5, which terminates at an intake opening 6. Such embodiments are known.

A gravity valve 7 is disposed in the intake opening and is constituted by a conical valve member 8, which cooperates with a seat which is constituted by the conical wall 9 of the sample vessel above the intake opening 6 and which is provided with an actuating member 10, which protrudes out through the intake opening 6 and is bare relative to the latter.

Under a pressure applied to the top 11 of the valve member the latter is forced against its seat. The actuating element protrudes downwardly. The valve can be opened at any time when the end 12 of the outwardly protruding actuating member 10 is forced against an abutment surface. The top 11 preferably constitutes an upwardly tapering cone.

The valve member 8 can be inserted or thrown in from above through the opening 4. For this reason the valve member can be removed from the sample vessel 3 after an examination and can be used again when it has been cleaned or disinfected.

The embodiment of FIG. 1 is shown merely by way of example.

FIG. 2 is a greatly enlarged view showing the bottom end portion 13 of a sample vessel 3 which is known per se. In that embodiment the valve member 3 is provided with an actuating rod 10, which is bare relative to the bottom intake opening 6. In the special embodiment shown in FIG. 2 the valve member 8 comprises a cone 14 having an apex 15 which faces into the interior of the sample vessel 3. Said parts thus constitute an extension 33, which is directed into the interior of the sample vessel. The base rim 16 of that cone 14 constitutes a seating surface for sealing the sample vessel under the action of an internal pressure or under the action of the weight of the valve member 8. The base rim 16 may be elastically deformable and adaptable. In that embodiment it is essential that the actuating rod protrudes with a clearance through the bottom intake opening 6.

The valve member shown in FIG. 2a is generally designated 45 and comprises an enlarged intermediate seating portion 35 formed with a peripheral annular flute or groove 36 for receiving an additional resilient sealing element 37. At both ends of the intermediate seating portion, i.e., above and below the latter, the valve member comprises elongate conical portions 38, 39, which will be described hereinafter with reference to FIG. 6.

Figure 3:
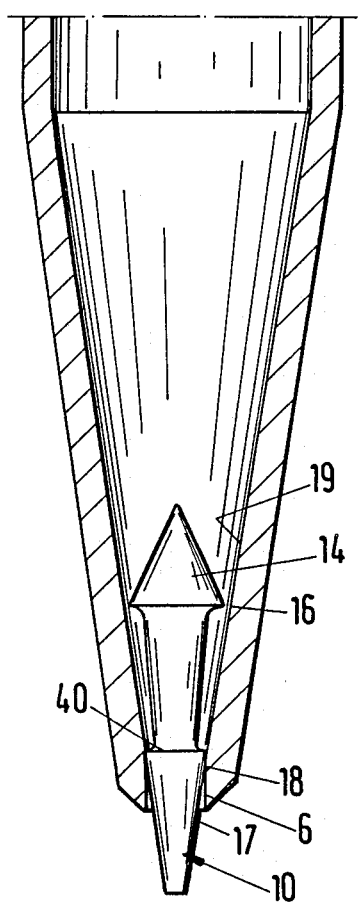
FIG. 3 is a fragmentary view which is similar to FIG. 2 and shows a further embodiment.

A similar view is apparent from FIG. 3 with the difference that the actuating rod 10 has a conical external surface 17 which constitutes a portion of a cone and which is adapted to seat on a mating conical inside surface portion 18 provided in the sample vessel in or above the bottom intake opening, which is designated 6 in FIG. 2. In that embodiment the top cone 14 serves as a pilot element, which has such a backlash that it will not compete with the seating at the bottom. In that case the base rim 16 of the cone 14 will be bare relative to the inside surface 19 of the sample vessel. The top cone serves only to effect an approximate alignment of the valve member proper. In dependence on the wall thickness of the sample vessel the intake opening 6 may be defined by a cylindrical rim if the hollow conical inside surface of the vessel does not extend as far as to the bottom edge. Particularly because the drawings are greatly enlarge, it is apparent from them that the cylindrical surfaces defining the intake opening 6 are very short in practice. Whereas said openings have small tolerances, the dimensions of the conical top inside surface may vary within wider limits. In that respect, FIG. 3 constitutes a desirable embodiment, in which the rim 40 at the top end of the conical actuating rod 10 constitutes particularly desirable means for effecting a seal. FIG. 4 shows that the sample vessel may have a conical inside surface which extends continuously as far as to the bottom rim of the opening 6.

Figure 5:
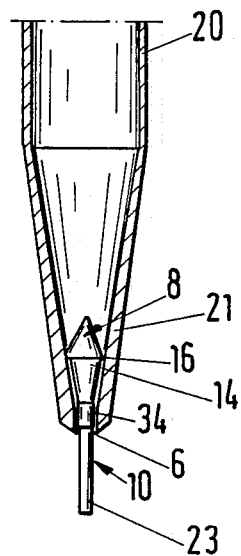
FIG. 5 is a fragmentary view which is similar to FIG. 4 and illustrates a different embodiment.

FIGS. 4 and 5 are fragmentary views showing different sample vessels in which the intermediate wall portion 20 is cylindrical and conical, respectively. The sample vessel having a cylindrical intermediate wall portion has a conical flaring portion also at its top end, not shown, so that the vessel can be fitted on a pipette.

The tapering bottom portion 21 above the intake opening 6 contains a gravity valve 7, which has a seating surface 22, which cooperates with the intake opening 6 of FIG. 4. From that seating surface 22 the actuating rod 10 extends downwardly. The seating surface 22 has a downwardly tapering, conical, shape and has such a size in cross-section that a seal is effected in the intake opening 6. The top portion of the valve member 7 is constituted by an upwardly flaring cone 14, which at its base is bare relative to the inside surface of the sample vessel when the valve is closed. That cone 14 constitutes a pilot element and a weighting body because those portions which are disposed adjacent to the intake opening 6 are very small in cross-section.

In the embodiment shown in FIG. 5 the valve member 8 has a base rim 16 for sealing engagement with the inside surface of the sample vessel and the actuating rod 10 comprises below the valve member 8 a portion 34 which defines only a small clearance with the intake opening. The portion 34 may be enlarged relative to the outwardly protruding portion 23 of the actuating rod 10 proper. The portion 34 is so short that when the valve member 8 has been pushed inwardly to open the valve, the portion 34 will be disposed outside the intake opening so that the larger difference between the cross-sections of the end portion 23 of the actuating rod 10 and of the intake opening 6 will be fully effective for draining the liquid from the vessel.

In the embodiment shown in FIG. 5 the seating portion of the valve is constituted by the base rim 16 of the cone 14. That base rim 16 may be designed as described hereinbefore. But in the embodiment shown in FIG. 5 the portion 34 of the actuating member 10 will effect a lateral guidance in the intake opening 6 shortly before and as the valve is closed so that an excessive canting will be avoided.

Figure 6:
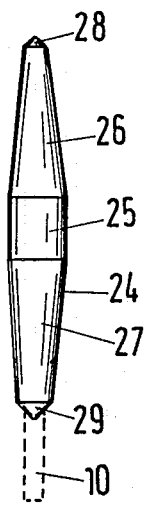
FIG. 6 is a side elevation showing a special embodiment of a valve member which can be inserted into a sample vessel of any of the embodiments described hereinbefore.

The valve members shown in the previously discussed figures can be understood in view of the drawing. FIG. 6 shows a specially designed valve member 24, which may be made from any of the materials stated hereinbefore. That valve member 24 has a cylindrical intermediate portion 25 and two conical portions 26, 27, which extend axially from said cylindrical portion 25 and have different included angles. Owing to its symmetrical or quasisymmetrical shape that valve member cannot be inserted in a wrong orientation so that its use will be simplified and the vessel will be more reliable in operation.

The conical portions terminate in conical tips 28, 29, which will assist the draining of sample liquid in the sense outlined hereinbefore.

When such a valve member is used, one of the conical portions 26, 27 serves as an actuating element of that valve member and comprises at least one rodlike portion 10, which constitutes an extension of the associated conical tip 28, 29 at least at that end at which the conical shape prevents the valve member from moving out through the intake opening.

As has been explained hereinbefore the handling can be facilitated in that such valve member can be inserted in different orientations into different vessels having intake openings which have different tapers. The conical seating portions 26, 27 of the valve member can seat on corresponding mating conical inside surfaces of the sample vessel.

Figure 7:
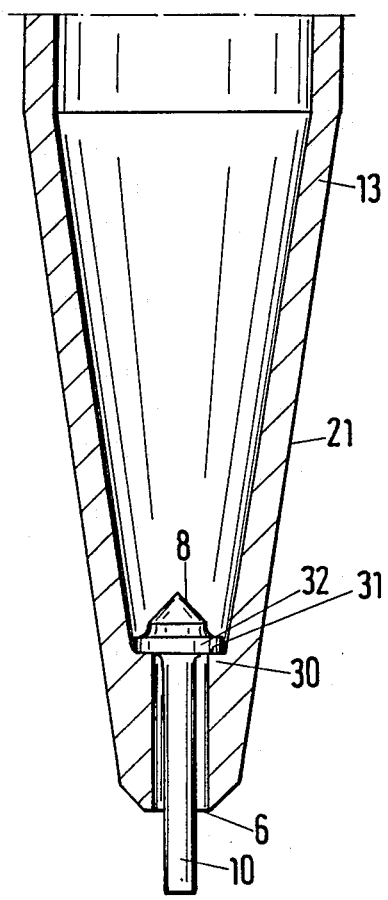
FIG. 7 is a fragmentary vertical sectional view showing a special embodiment of a sample vessel provided with a special gravity valve.

FIG. 7 shows the conical end portion 13 of a sample vessel or sample taking element. That conical end portion is provided at its bottom with the intake and discharge opening 6. In the special embodiment shown in FIG. 7 the inside surface of the sample vessel is formed above the intake opening 6 with an inwardly directed step 30, which may optionally be constituted by an annular flange having a flat top 31, and the valve member 8 consists of a gravity valve having a cylindrical disc 32 for seating on the flat top surface 31. The provision of a step has the advantage that cavities which might be involved where an annular flange is used will be avoided so that in the illustrative embodiment the actuating member 10 extends through a cylindrical opening. In that embodiment the downwardly extended actuating rod 10 is also smaller in cross-section than the opening within the step and in the adjoining lower portion extending as far as to the intake opening 6, which serves also as a discharge opening.

Figure 8:
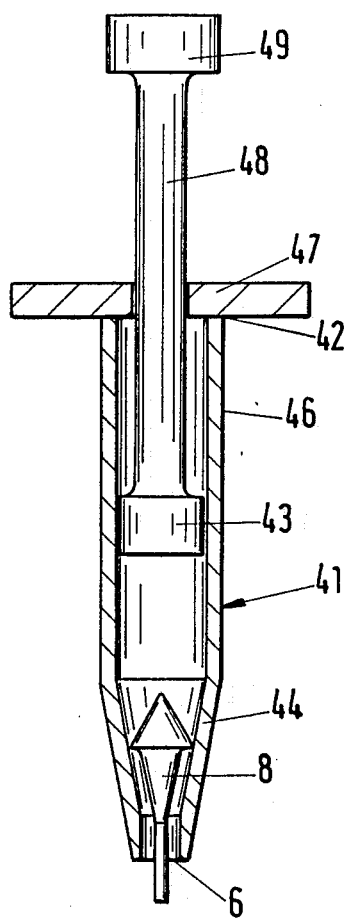
FIG. 8 is a diagrammatic perspective view showing a syringelike instrument provided with a sample holding element.

FIG. 8 is a diagrammatic view showing the sample taking element as a sealing end portion of a syringelike instrument 41, which has a cylindrical part 46 that is formed with the opening 42 and is provided on the outside with a mounting flange 47. That cylindrical part contains a piston 43, which is movable by means of a pipettelike metering device, in which the mounting flange 47 is fixed and in which the piston rod 48 is connected by a connector 49 to an actuator.

The syringelike instrument 41 is provided with a sample taking element 44, which in other respects corresponds to the tip of the sample taking vessels which have been discussed hereinbefore. The intake and discharge opening 6 is provided with a valve member, which is designated 8 as in FIG. 1.

I claim:

1. A movable valve member for a fillable sample taking vessel for handling a liquid sample, which vessel is relatively large in diameter at one end which has a first opening which is relatively large in cross-section, the vessel having a constricted second opening at its other end and a conical portion which tapers from a point that is spaced from said first opening towards said constricted second opening, said second opening constituting an intake and discharge opening, the valve member being provided in said conical portion adjacent to the intake opening and being freely movable for sealing said vessel adjacent to said intake opening, the valve member being part of a gravity valve and having a specific gravity which is higher than that of a liquid to be handled, a substantial portion of the valve member being inserted into said vessel through said first opening and being disposed in said vessel in said conical portion above said intake opening, said vessel being provided adjacent to said intake opening with a valve seat which faces said first opening and is engageable by said valve member to seal said intake opening, said valve member having a cylindrical intermediate portion and at opposite ends of said cylindrical intermediate portion, conical portions which terminate in conical tips, one of said tips constituting an actuating element, additionally the valve member comprises an enlarged intermediate seating portion formed with an additional resilient seating element.

2. A member according to claim 1, and further comprising a peripheral annular flute or groove for receiving the sealing element.

3. A member according to claim 1, wherein the actuating element projects outward through the second opening.

4. A member according to claim 1, wherein said vessel comprises a cylindrical portion adjoining said first opening, and further comprising a piston inserted through said first opening and disposed in said cylindrical portion and having an outwardly protruding piston rod.

5. A member according to claim 1, wherein said valve seat is formed by an inwardly directed step which constitutes a portion of enlarged wall thickness inside the sample taking vessel, said step having a flat top surface in said vessel.

6. A member according to claim 1, wherein a valve seat is provided which is formed by a conical surface which flares upwardly toward said first opening, and a valve member is provided which has a conical portion which is adapted to be seated on said upwardly flaring conical surface of said valve seat, said conical valve seat being formed by an inside surface of a tapering wall portion of the sample taking vessel.

7. A member according to claim 1, wherein the valve body is provided with an extension above the seating portion for engaging the valve seat, said extension extending into the interior of the sample taking vessel and said extension having a rim which, when the valve is closed, is disposed at such a cross-section of the sample taking vessel that said rim is bare relative to the wall of the sample taking vessel.

8. A member according to claim 7, wherein said extension is formed by a cone having an apex which faces the top end of the sample taking vessel.

* * * * *